(12) United States Patent
Felden et al.

(10) Patent No.: US 9,931,604 B2
(45) Date of Patent: Apr. 3, 2018

(54) APPARATUS FOR PERFORMING SONICATION

(71) Applicant: Merck Patent GmbH, Darmstadt (DE)

(72) Inventors: Luc Felden, Andolsheim (FR); David Lehmann, Andolsheim (FR); Marisa Hohnadel, Schiltigheim (FR); Sebastien Jouette, Molsheim (FR)

(73) Assignee: MERCK PATENT GMBH, Darmstadt (DE)

( * ) Notice: Subject to any disclaimer, the term of this patent is extended or adjusted under 35 U.S.C. 154(b) by 129 days.

(21) Appl. No.: 14/773,796

(22) PCT Filed: Feb. 20, 2014

(86) PCT No.: PCT/EP2014/000451
§ 371 (c)(1),
(2) Date: Sep. 9, 2015

(87) PCT Pub. No.: WO2014/139630
PCT Pub. Date: Sep. 18, 2014

(65) Prior Publication Data
US 2016/0023174 A1    Jan. 28, 2016

(30) Foreign Application Priority Data

Mar. 15, 2013  (EP) ..................................... 13290065
Aug. 22, 2013  (EP) ..................................... 13290200

(51) Int. Cl.
*B01F 11/00*    (2006.01)
*B01F 11/02*    (2006.01)
(Continued)

(52) U.S. Cl.
CPC .......... *B01F 11/02* (2013.01); *B01F 11/0266* (2013.01); *G01N 1/28* (2013.01);
(Continued)

(58) Field of Classification Search
CPC .................. B01F 11/02; B01F 11/0266; B01F 2215/0037; G01N 1/28; G01N 2215/0037
See application file for complete search history.

(56) References Cited

U.S. PATENT DOCUMENTS

| 4,983,523 A | 1/1991 | Li et al. |
| 6,619,586 B1 | 9/2003 | Barnes, III |

(Continued)

FOREIGN PATENT DOCUMENTS

| CN | 2581058 Y | 10/2003 |
| CN | 1688382 A | 10/2005 |

(Continued)

OTHER PUBLICATIONS

Chinese Search Report dated Aug. 3, 2016, issued in corresponding Chinese Application No. 201480015880.8, 2 pages.
(Continued)

*Primary Examiner* — Anshu Bhatia
(74) *Attorney, Agent, or Firm* — Millen, White, Zelano, Branigan, P.C.

(57) ABSTRACT

An apparatus for performing sonication on liquid samples comprises a rack for holding an array of sample vials, an ultrasonic probe with an arrangement of recesses corresponding to the array of sample vials and adapted to respectively receive and contact an outer surface of a bottom portion of a respective one of the sample vials, and a counter-holder with an arrangement of pushing members corresponding to the array of sample vials and adapted to respectively apply a force to a respective one of the sample vials so as to push the bottom portion of each vial into contact with the associated recess of the probe. The apparatus can be used in a method of preparing a sample for detection of cell components (e.g. cell analyte, proteins, nucleid acids etc.) and applying sonication within certain parameter ranges which can provide a universal lysis
(Continued)

method that can be applied to a large variety of cells or organisms like all bacteria, viruses, spores, yeast and mold within the same apparatus and process.

18 Claims, 2 Drawing Sheets

(51) Int. Cl.
G01N 1/28 (2006.01)
G01N 35/00 (2006.01)
(52) U.S. Cl.
CPC ............ B01F 2215/0037 (2013.01); G01N 2035/00554 (2013.01)

(56) References Cited

U.S. PATENT DOCUMENTS

| | | |
|---|---|---|
| 6,686,195 B1 | 2/2004 | Colin |
| 7,781,206 B2 | 8/2010 | Hukari et al. |
| 8,240,213 B2 | 8/2012 | Donaty |
| 8,342,736 B2 | 1/2013 | Luotola et al. |
| 8,450,095 B2 | 5/2013 | Hukari et al. |
| 8,662,735 B2 | 3/2014 | Luotola et al. |
| 2007/0238090 A1 | 10/2007 | Hukari et al. |
| 2008/0308404 A1 | 12/2008 | Luotola et al. |
| 2009/0151459 A1 | 6/2009 | Donaty |
| 2010/0122586 A1 | 5/2010 | Misu |
| 2011/0014673 A1 | 1/2011 | Hukari et al. |
| 2011/0151577 A1 | 6/2011 | Zhang |
| 2013/0087445 A1 | 4/2013 | Luotola et al. |
| 2014/0113277 A1* | 4/2014 | Thomas ............... G01N 29/032 435/5 |

FOREIGN PATENT DOCUMENTS

| | | |
|---|---|---|
| CN | 101175557 A | 5/2008 |
| CN | 102131913 A | 7/2011 |
| CN | 202460532 U | 10/2012 |
| EP | 0337690 A1 | 10/1989 |
| JP | 2002-540783 A | 12/2002 |
| JP | 2009-25248 A | 2/2009 |
| JP | 2012-501177 A | 1/2012 |
| WO | 2006119932 A1 | 11/2006 |

OTHER PUBLICATIONS

English translation Abstract of CN102131913A published Jul. 20, 2011 (2 pages).
English translation Abstract of CN101175557A published May 7, 2008 (2 pages).
English translation Abstract of CN202460532U published Oct. 3, 2012 (1 page).
English translation Abstract of CN1688382A published Oct. 26, 2005 (2 pages).
English translation Abstract of CN2581058Y published Oct. 22, 2003 (1 page).
International Search Report from PCT Application No. PCT/EP2014/000451 dated May 16, 2014.
Translation of Japanese Office Action corresponding to JP 2015-561970, dated Dec. 13, 2017.

* cited by examiner

APPARATUS FOR PERFORMING SONICATION

The present invention relates to an apparatus for performing sonication on liquid samples, preferably in the field of biology, molecular biology, biotechnology, biochemistry, general chemistry, food and beverage industry, pharmaceutical industry and for use in diagnostic applications in general. The invention moreover relates to a method of preparing a sample for detection of cell components using the apparatus for performing sonication.

Sonication is used in the above fields for a number of uses such as mixing, solubilization, driving chemical reactions, tissue homogenization, cell operation and uses, shearing of biological molecules such as DNA as well as cleaning, plastic welding, etc. Sonication in these fields (except for plastic welding) is normally performed in bath sonicators where water transfers the sonic energy from a transducer to a sample, or with probe sonicators where a metal probe immersed into the sample applies the sonic energy to it. Bath sonication is limited in the amount of energy it transfers to the sample. Probe sonication could supply substantial energy but is limited to one sample at a time or one sample per probe. Furthermore, immersing the metal probe(s) into the sample necessarily contaminates the metal probe and requires costly cleaning.

Samples to be processed by sonication may comprise bacteria, cells, viruses and other materials containing the nucleic acids to be assayed in a suitable solution which is added in a predetermined volume to the sample container.

Most of the current devices for performing sonication on liquid sample are limited as to the minimum volume of sample liquid they can treat or process at one point of time, thereby providing only a limited throughput, or suffer from other disadvantages like excessive cleaning requirements after use.

The document US 2009/0151459 A1 discloses a system and method for ultrasonic sample preparation which includes a cylindrical sample container formed from a polymeric material and having a wall defining an outer peripheral side surface and an inner volume of between about 1 ml and about 25 ml for containing a sample material. An external converter is provided which converts AC electricity to mechanical vibrations in the ultrasonic range, and an ultrasonic probe is provided to be in contact with the outer peripheral surface of the sample container. The ultrasonic probe is in communication with a converter and transmits the mechanical vibrations to the wall of the sample container and thereby to the inner volume to excite and mix the sample material in the container. The probe has a probe portion which is not inserted into the sample container but makes intimate contact with the peripheral side wall of the sample container. This prior art is a manually operated system and is restricted to sonication of a single sample in a single sample container at one time.

The document EP 0337690 A1 discloses another method and apparatus for preparing sample nucleic acids comprising non-invasive sonication of the sample contained within a sample container brought into physical contact with an elongated vibrating ultrasonic tip of a sonicator resonating at a frequency of 40 kHz or greater. The ultrasonic transducer is mounted on a frame member, which in turn is mounted upon a base located within a housing. The ultrasonic transducer is mounted upon a pneumatic cylinder for controlling the force of the ultrasonic tip against a disposable cuvette serving as a container for the sample liquid. The cuvette is maintained against the ultrasonic tip by a force retainer which slidably engages the top of the cuvette. To maintain the contact between the ultrasonic tip and the cuvette, the apparatus applies a pressure of $6 \times 10^4$ to $2 \times 10^5$ $Nm^{-2}$ through energizing the pneumatic cylinder. This apparatus is also a one-sample-at-a-time apparatus and is therefore not suitable for high-throughput applications.

The document US 2007/0238090 A1 discloses another system and method for processing a biological liquid sample for use in lysing viruses or biological cells for analysis using biological assay systems. The sample volume to be treated by this system is in the range from about 1 ml to 10 ml and the sample is processed by applying pressure and either sonic energy or thermal energy to the sample. To this end the apparatus has a specific vial that is cylindrical and has an internal chamber for receiving the sample. The vial has an open upper end into which a plug or insert for sealing the open upper end is inserted and a retaining cap for holding the plug in the vial by a threaded engagement with the upper external end portion of the vial. A heater coil surrounds the lower end of the vial and a sonication head in the form of an elongated tip is located so as to face and contact a flat lower bottom end face of the vial.

In one further embodiment the document US 2007/0238090 A1 discloses an apparatus where the above structure with a specific vial and the associated elongated sonication head is multiplied so that the plurality of different samples can be simultaneously processed. This system has a multi-well plate having a plurality of wells or chambers, each for receiving a sample of predetermined size, a plug plate having a plurality of plugs or plungers projecting from one face for sealing engagement in a respective aligned well in the multi-well plate, and a locking or latching mechanism for securing the two plates together when each plug is fully inserted into the respective well. A heater is provided for heating the sample in each well and an ultrasonic device having a plurality of elongated tips equal to the number of wells in the plate is used to apply ultrasonic waves to the sample in each well in that the multi-probe sonication device is aligned with the lower ends of the wells and moved towards the wells until each probe contacts the flat bottom end face of the respective aligned well.

This embodiment is improving the system in a sense that it allows the simultaneous processing of a larger number of samples but it is a very complicated arrangement requiring especially the multitude of ultrasonic probe tips.

It is the object of the present invention to provide an apparatus for performing sonication on plural liquid samples which is suitable to perform the sonication on a number of samples simultaneously and which is more simplified and more robust than prior devices. Furthermore, it is an object of the invention to provide a method of preparing a sample for detection of cell components by means of sonication that can effectively perform a lysis on a number of samples in a large application field.

To solve this problem the present invention provides an apparatus for performing sonication on a liquid sample as defined in claim 1 and a method of preparing a sample for detection of cell components using such an apparatus as defined in claim 11. Preferred embodiments of the apparatus and of the method are defined in the dependent claims.

The apparatus of the invention for performing sonication on liquid samples comprises a rack for holding an array of sample vials, an ultrasonic probe with an arrangement of recesses corresponding to the array of sample vials and adapted to respectively receive and contact an outer surface of a bottom portion of a respective one of the sample vials, and a counter-holder with an arrangement of pushing members corresponding to the array of sample vials and adapted to respectively apply a force to a respective one of the sample vials so as to push the bottom portion of each vial into contact with the associated recess of the probe.

The method of preparing a sample for detection of cell components according to the invention comprises the steps of providing the sample in a sample vial, placing the sample vial in the apparatus of the invention, performing sonication on the sample in the sample vial by the apparatus using the following parameters to effect a lysis of the sample: applying a mechanical stress in between the sample vial and the probe of 0.1 to 1 N/mm$^2$, applying a peak-to-peak amplitude of vibration of 2 to 10 μm, and applying a frequency of vibration of 20 to 100 kHz.

One advantage of the apparatus is that lysis by way of sonication can be performed on plural samples in the array simultaneously, wherein the samples are received in standard vials or containers that are commonly used as consumables in the field of biochemistry, general chemistry, food and beverage industry, pharmaceutical industry and for use in diagnostic applications in general, to carry out microreactions in the microliter-range. These vials typically comprise conical laboratory tubes, so called 50 ml conical centrifuge tubes or round-bottom-tubes, 1.5 ml or 2 ml microcentrifuge tubes, that are individually held in the rack, or microtiter plates that combine an array of wells or test tubes in an integral plate, and are typically made from plastics materials including PP (polypropylene), PS (polystyrene), PC (polycarbonate), PET (polyethylene) or thin glass.

By allowing sonication of the samples in such standard vials or containers, even very small amounts of sample liquid can be lysed efficiently because the probe by way of its arrangement of recesses corresponding to the array of sample vials respectively receives and contacts an outer surface of the bottom portion of each respective one of the sample vials. The small amount of the sample liquid commonly collects at the bottom portion of each such vial, which is typically conical or round or semi-spherical. The recess of the probe surrounds that bottom portion not only at the lower end face but also at a part of the length above the bottom end and thus maximizes the surface area and encircles the entire liquid volume. Thus, more energy can be transferred to the sample without the danger of melting or breaking the vial tube and without requiring cooling of the vials during sonication. Moreover, the energy is more homogenously distributed and applied to the complete volume of the sample.

The indirect sonication from the outside of the vial avoids contact of the ultrasonic probe with the sample liquid and the fact that an array of plural sample vials can be sonicated simultaneously within the rack by the common ultrasonic probe provides a fast result and a high throughput for large quantities of samples to be processed while involving only a limited variation between the samples in the array.

The apparatus moreover provides an easy-to-use system since the holder of the rack for the samples is designed to be moved into contact with the ultrasonic probe, which may stand still in the apparatus, so that there is a defined movement by way of a simple mechanical mechanism that increases safety for the users operating the apparatus. The simple mechanical arrangement provides the possibility of automating the transport of the rack holding the array of sample vials into the operating position which could be inside a substantially closed housing sealed from the environment. Therefore, the apparatus does not require manual handling steps during the process and only an arrangement of the vials into the rack of the apparatus as a preparatory step.

In that the ultrasonic probe is an integral block that has an array or arrangement of recesses corresponding to the array of sample vials and formed to respectively receive and contact an outer surface of a bottom portion of a respective one of the sample vials, i.e. in that the shape of the recesses mimics the shape of the bottom of the vials, the contact area with the outer surface of the vial is maximized and transfer of ultrasonic energy is concentrated on that part of the vial where the sample liquid collects even in case only very small amounts of sample liquid in the microliter-range are treated. Thereby, even very small amounts of sample liquid in the range of 20 μl to 1 ml can be sonicated using standard vials or containers available as consumables in the industry.

The structure of the ultrasonic probe also provides the advantage that the sonication energy is homogeneously distributed with respect to all the sample vials in the array so that the deviation between energy amounts applied at the respective positions is small and the comparability of the results throughout the entire array is secured.

A particularly advantageous embodiment is one where the plural recesses in the ultrasonic probe are each configured so as to match different bottom configurations of at least two different vials. This considerably increases the universal application of the apparatus and the speed of the sonication because no modification of the apparatus is required if a different type of vials/containers is to be processed from one batch to the next.

Since the ultrasonic probe is provided with the arrangement of recesses and otherwise forms an integral block for all the sample vials to be processed in the apparatus, the structure is simple and the excitation of each liquid sample is comparable within narrow ranges. This facilitates processing of larger numbers of samples and makes results more comparable. Furthermore, the simple structure of the ultrasonic probe facilitates cleaning of the apparatus in cases where sample liquid spills out from the vials/containers.

The method of preparing a sample for detection of cell components of the invention using the apparatus of the invention and applying sonication within the parameter ranges of claim 11 provides a universal lysis method that can be applied to a large variety of cells or organisms like all bacteria, viruses, spores, yeast and mold within the same apparatus and process. This reduces the number of different procedures that have to be implemented and documented in a laboratory and makes the procedures more simple and comparable to each other.

These and other aspects will become apparent from the description of a preferred embodiment below in connection with the attached drawing. In this drawing:

Figure 1:
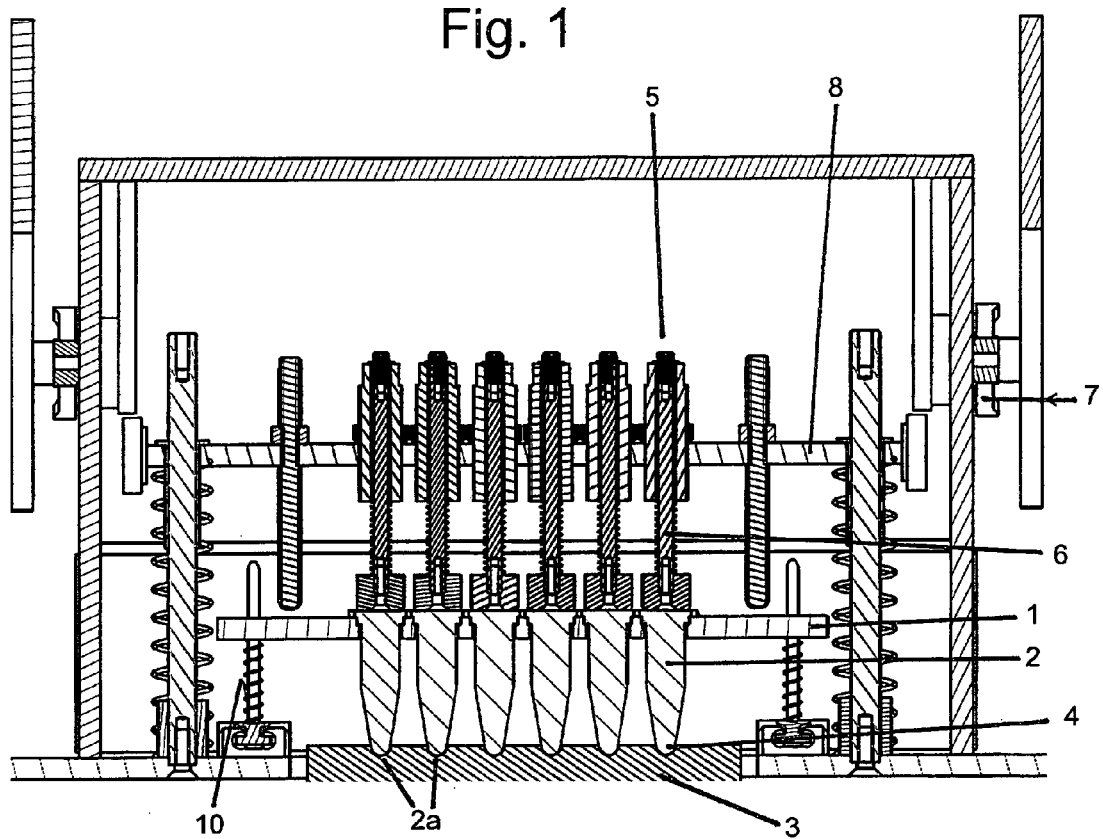
FIG. 1 shows a perspective schematic view of an exemplary embodiment of the apparatus of the present invention.
Figure 2:
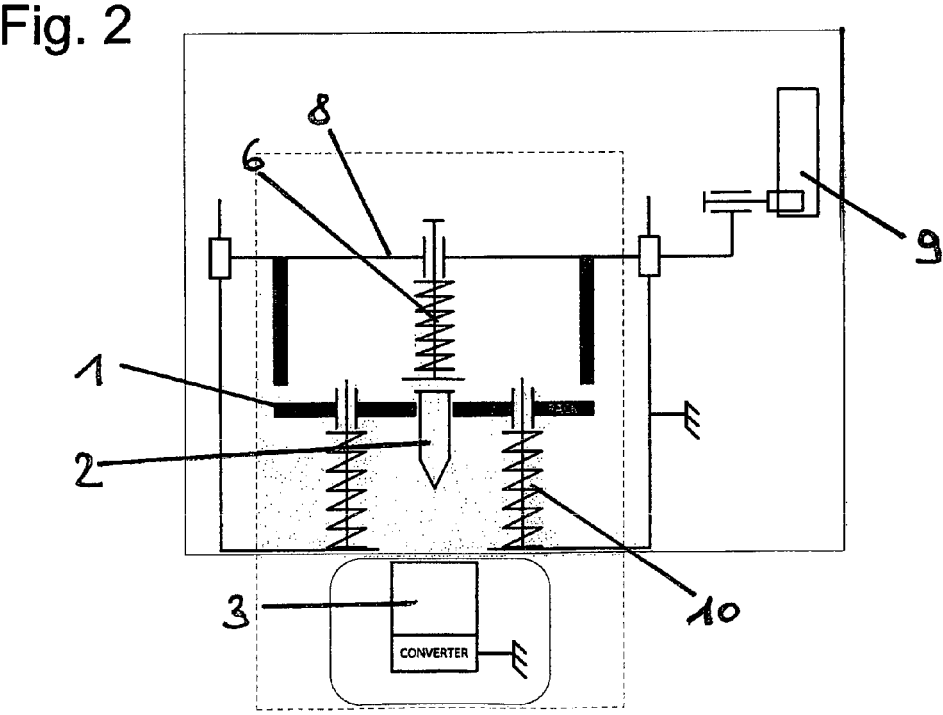
FIG. 2 shows the kinematic diagram of the apparatus of FIG. 1.

The basic configuration of the apparatus of the invention is shown in FIGS. 1 and 2. The apparatus has a rack 1 for holding an array of sample vials 2 and an ultrasonic probe 3 with an arrangement of recesses 4 corresponding to the array of sample vials and adapted to respectively receive and contact an outer surface of a bottom portion 2a of a respective one of the sample vials when the probe and rack are aligned and brought into a working position shown in FIG. 1. The probe 3 is cooperating with a converter that produces the ultrasonic vibration and transmits it to the probe.

The rack 1 is supported so as to be movable in the direction of the center axes and is preferably elastically biased in a direction towards pushing members 6 of a pushing mechanism 7 of a counter-holder 5 for applying a holding or contact force. A moving mechanism (not shown) is preferably provided in the apparatus for moving the rack between a position outside of a housing of the apparatus and a position inside the housing aligned with the ultrasonic probe. Thus, an operator only has to place the vials with the samples into the rack or place the entire rack with the vials on the moving mechanism. These motions can be performed by hand but can also be automated, for example by dedicated or programmable manipulators or robots. After initiation of the process (i.e. by pushing a "start"-button) the rack is automatically moved into the housing, preferably by a horizontal movement, and sonication is performed while the operator is shielded from the process. After the preset sonication time has lapsed, the rack is again moved out from the housing by the moving mechanism for further handling of the vials.

The counter-holder 5 has an arrangement of pushing members corresponding to the array of sample vials and adapted to respectively apply a force to a top of a respective one of the sample vials 2 so as to push the bottom portion of each vial into tight contact with the associated recess 4 of the probe 3 with a defined pressure (force per surface area). The pressure is sufficiently high that a maximum of ultrasonic energy is transferred to the sample in the vial and not to the vial itself in order to avoid the melting of the vial material (i.e. polypropylene) at the interface. A loss of contact would in fact create a shearing at the interface which would increase the temperature. On the other hand, a too high contact pressure would demand too much power from the power converter in order to maintain a constant vibration amplitude and could create stress at the border of the vial which could have the same negative consequences as loss of contact.

The force for creating the contact pressure could be created in a number of different ways in the apparatus. In the shown preferred embodiment the pushing members are preferably in the form of pushrods 6 that are arranged and held in a common platform 8 to apply the force to the top portion of the respective associated vials and to be moved together by means of a drive mechanism 9. A different configuration of the pushing members and a different place where the force is introduced into the vials are feasible. In a preferred embodiment (not shown) the array of pushing members is exchangeable to accommodate a different array of sample vials and/or sample vials with different configuration.

The pushrods 6 are preferably designed such that the force is adjustable and/or the pushrods are elastically biased towards the vials. This can be achieved by pre-tensioned springs of which the pre-tension is adjustable to tune the force applied to the respective vial.

The positioning mechanism 9 is provided to selectively move the platform 8 and thereby engage the arrangement of pushing members 6 with the vials. This positioning mechanism 9 comprises the platform 8 for holding the array of pushing members 6. The platform 8 is supported so as to be at least movable in the direction towards and away from the probe 3 and a drive mechanism 9 for repeatedly alternatingly moving the platform 8 between these positions and apply the same holding force may comprise a cam/follower system with a gear and a drive motor as shown in FIG. 2. Other drive mechanisms including electric, hydraulic or pneumatic drive actuation are feasible. The pushrods 6 could also be biased by electric or hydraulic cylinders (not shown).

The arrangement in the apparatus is generally such that the center axes of the associated recesses and pushing members are aligned and are concentric with the associated sample vials in the array, at least when the force is applied and the sonication is started.

Figure 3:
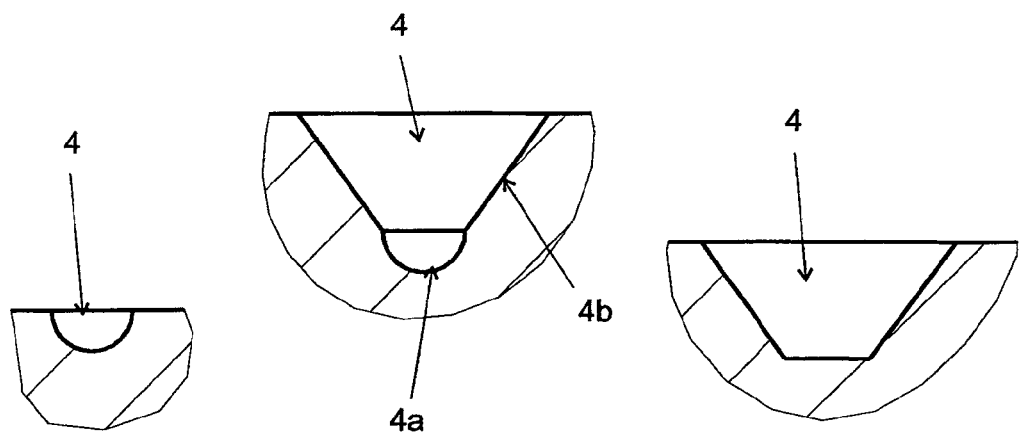
FIG. 3 shows a probe in cross section with different exemplified types of recesses representing different preferred embodiments and enlarged cross-sectional views of the individual recesses within the ultrasonic probe of the apparatus of the invention.
Figure 3:
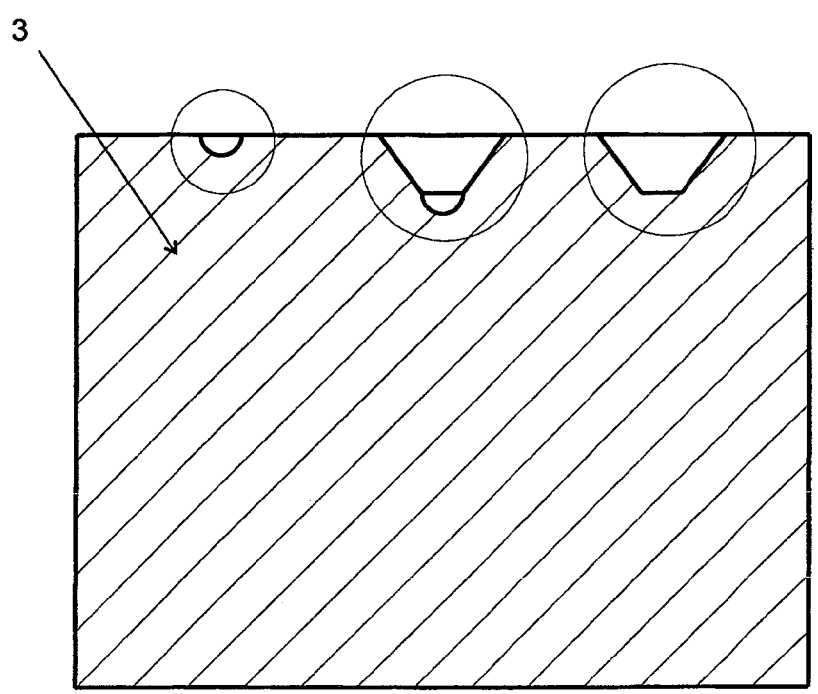

The recesses 4 of the integral block-like ultrasonic probe 3 of the apparatus as shown, for example in FIG. 3 are an important aspect of the invention. The recesses are formed to match, at least to a certain extent, a bottom configuration of the bottom portion 2a of the vials 2 to be used in the array, wherein the recesses are preferably rotational symmetrical about a center axis and, depending on the type of vial used in the apparatus, preferably either hemispherical or conical as shown in FIG. 3a. Thus, the apparatus can be used in connection with common standard reaction vessels or vials or containers which could be grouped into small vials/containers having a typical rated volume or size in the range of 1.5 ml to 2 ml, i.e. so-called Eppendorf cups, that typically have a snap cover or conical seal or silicone seal, or large vials/containers which are typically in the rated volume in the range of 15 ml to 50 ml that have a snap or screw cover and that are, for example, available as 50 ml conical centrifuge tubes or 96-well plates with 200 µl wells.

The vials can be individual containers as described above or microtiter plates that combine an array of wells or test tubes in an integral plate. All these containers are typically made from plastics materials including PP (polypropylene), PS (polystyrene), PC (polycarbonate), PET (polyethylene), or from thin glass. The small types of vials typically have a small hemispherical tip end and the larger types of vials have a conical lower end but different configurations are possible. As shown in FIG. 3a the recesses of the ultrasonic probe of the invention are mimicking these bottom configurations of the vials that are typically used in the laboratory environment. Thereby, the contact area with the outer surface in the bottom section is maximized and the contact area is not only restricted to the axial bottom surface but extends further upward so that the contact area between the recess and the vial surrounds the lower bottom end where the small volumes of sample liquid collect.

In a particularly preferred embodiment that is shown in FIG. 3b, each recess is configured so as to match different bottom configurations of at least two or even more different vials. Such a structure as shown in FIG. 3b combines the semi-spherical contour for the small types of vials at the lower portion with the conical configuration of the large type of vials adjacent to the bottom end in one recess. Here, too, different configurations can be implemented that provide maximum contact area with the different configurations.

The apparatus of the invention can be applied universally to a large number of lysis tasks on liquid samples in the field of biology, molecular biology, biotechnology, biochemistry, general chemistry, food and beverage industry, pharmaceutical industry and for use in diagnostic applications in general. In that the common sample vials/containers as described above can be accommodated in the apparatus and in that the parameters of the sonication process like holding force on the sample vials, peak-to-peak amplitude of vibration, and frequency as well as sonication time can be set in the apparatus, a wide variety of applications like mixing, sono-chemistry, and sample preparation for diagnostics can be carried out.

A particularly advantageous effect is obtained by using the above described apparatus in a method of preparing one or more sample(s) for detection of cell components (e.g. cell analyte, proteins, nucleic acid (NA), etc.) which thus comprises the steps of providing each sample in a separate sample vial, placing the sample vials in the apparatus, performing sonication on the samples in the sample vials simultaneously by the apparatus using the following parameters to effect a lysis of the samples:

- applying a holding mechanical stress in between the sample vials and the probe of 0.1 to 1 $N/mm^2$ (preferably 0.26+/−0.05 $N/mm^2$ for 1.5 ml microcentifuge tubes and 0.1+/−0.01 $N/mm^2$ for 50 ml conical centrifuge tubes);
- applying a peak-to-peak amplitude of vibration of 2 to 10 μm (preferably 4 μm for small tubes and 10 μm for large tubes); and
- applying a frequency of vibration of 20 to 100 kHz (preferably 20 kHz+/−100 Hz for small and large tubes).

The sonication time is around 3 minutes for small and large tubes. The method is able to crack all bacteria, viruses, spores, yeasts and mold without destroying their NA when performed in the appropriate buffer medium, i.e. guanidine buffer.

The above defined parameter ranges turned out to cover a wide variety of sonication applications using the apparatus of the invention. A controller can be provided in the apparatus for allowing setting of the respective values within the ranges through a suitable operator interface and for controlling the components in the apparatus so that the sonication is effected within the set values. Further, the controller can also effect the automated transfer of the rack into and out from the apparatus as described above by activating the respective drive mechanisms in the apparatus in a predefined manner.

EXAMPLES

Example 1: Demonstration of the Lysis Efficiency on Microorganisms 1.1. Experimental Protocols
Preparation and Lysis of the Strains For each tested microorganism, few CFUs (colony forming units) from plate cultures are re-suspended in peptone salt diluent to a defined OD value. Ten-fold serial dilutions are realized.

Then, $10^4$ CFUs are spiked in lysis buffer (guanidine hydrochloride 1M, NLS 0.5%, 5 mM Tris pH 8, EDTA 0.5 mM). The total volume of the lysis solution is 500 μL. 10 replicate tests are realized.

The samples are sonicated with the apparatus according to the present invention in 1.5 mL sonication-resistant tubes (Eppendorf Safe-Lock Biopur) for ca. 3 minutes. A DNA purification step is immediately performed to isolate microorganism DNA in a real-time PCR compatible elution buffer.

DNA Purification

Magnetic DNA purification is performed to purify microorganism DNA using magnetic beads. 15 samples are purified simultaneously employing the KingFisher instrument (ThermoScientific ref.5400050) and the MilliPrep kit (Merck Millipore ref. MPRPMYC48).

Afterwards, the eluates are transferred into 1.5 mL tubes and centrifuged for 90 s at 10 000 g. If needed, the samples are stored at −20° C. and thawed before performing the specific real-time DNA amplification.

Specific Real-Time DNA Amplification and Detection

Except for *L. monocytogenes* and *E. coli*, specific real-time SYBR Green PCR assays are performed. A 15 μL PCR mix per reaction is prepared with 2× concentrated QuantiTect® SYBR® Green PCR kit (Qiagen) and 0.5 μM of specific primers. Then, 10 μL of each sample are added to each well. Negative controls (10 μL of water) and positive controls (1-100 ng of the tested microorganism gDNA) are incorporated in each run. Two PCR replicate tests per purified sample are realized.

The PCR plates (Twintec plate, Eppendorf) are sealed (Microseal® film, Bio-rad) and centrifuged for 2 minutes at 1700 rpm. The PCR assays are performed on the Mastercycler epgradient realplex$^2$ (Eppendorf) instrument.

For *E. coli*, a specific real-time TaqMan PCR assay is performed. A 15 μL PCR mix per reaction is prepared with 2× concentrated QuantiFast™ PCR kit (Qiagen), 0.1 μM of specific primer and 0.08 μM of a specific probe. Then, 10 μL of each sample are added into each well, with negative and positive controls. Two PCR replicates per purified sample are realized. The PCR plates and assays are performed as described above.

The *L. monocytogenes* test is performed, using the FoodProof® *Listeria Monocytogenes* Detection Kit (Biotecon Diagnostics). Two PCR replicates per purified sample are realized. The PCR plate (FrameStar®, 4titude) is sealed (QPCR Adhesive Clears, 4titude) and centrifuged for 2 minutes at 1700 rpm. The PCR assay is performed on the Stratagene Mx3005P (Agilent Technologies) instrument.

1.2. Results

| Strain | Av. Ct value ± stdev | Number of lysed CFUs |
|---|---|---|
| *E. faecalis* | 21.72 ± 0.508 | 8379 |
| *S. aureus* | 24.87 ± 0.384 | 9675 |
| *S. agalactiae* | 26.78 ± 0.340 | 16 380 |
| *S. epidermidis* | 25.33 ± 0.205 | 10 870 |
| *L. monocytogenes* | 29.13 ± 0.458 | 7664 |
| *P. aeruginosa* | 21.03 ± 0.192 | 16 550 |
| *S. enterica* | 23.23 ± 0.317 | 9113 |
| *E. coli* | 24.23 ± 0.194 | 7790 |
| *P. acnes* | 23.97 ± 0.204 | 5280 |
| *C. sporogenes* | 27.23 ± 0.599 | 5880 |
| Spores of *G. stearothermophilus* | 27.82 ± 0.479 | 10 110 |
| *Z. bailii* | 22.39 ± 0.77 | 12 830 |
| *C. albicans* | 21.66 ± 0.456 | 7976 |
| *C. neoformans* | 25.46 ± 0.503 | 9328 |
| *S. cerevisiae* | 28.78 ± 0.824 | 9250 |
| Spores of *A. brasiliensis* | 21.56 ± 0.563 | 5100 |

The data show that sonication can be considered as an efficient lysis method on Gram negative bacteria, Gram positive bacteria (including anaerobic bacteria), spores of bacteria, yeasts and spores of molds.

Example 2: Demonstration of the Lysis Linearity 2.1. Experimental Protocols

The linearity of the lysis using the sonication apparatus according to the present invention is tested by spiking and lysing 10/100/1000/10 000 CFUs of the tested microorganisms (prepared as described above). 5 replicates per tested concentration are realized. Purification and DNA amplification are realized as described above.

2.2. Results

| Strain | Av. Ct value ± stdev | Lysed CFUs | $R^2$ |
|---|---|---|---|
| S. enterica | 33.49 ± 0.98 | 8 | 0.9648 |
|  | 30.97 ± 0.53 | 116 |  |
|  | 27.32 ± 0.33 | 1160 |  |
|  | 23.68 ± 0.26 | 11 600 |  |
| S. aureus | 33.22 ± 1.065 | 13 | 0.9175 |
|  | 31.5 ± 1.064 | 157 |  |
|  | 28.40 ± 0.556 | 1570 |  |
|  | 24.91 ± 0.413 | 15 700 |  |
| C. albicans | 29.55 ± 1.226 | 9 | 0.9547 |
|  | 26.63 ± 0.868 | 86 |  |
|  | 23.85 ± 0.405 | 860 |  |
|  | 20.68 ± 0.425 | 8602 |  |
| A. brasiliensis | 36.99 ± 1.022 | 16 | 0.9866 |
|  | 32.23 ± 0.597 | 92 |  |
|  | 26.29 ± 0.440 | 920 |  |
|  | 20.69 ± 0.772 | 9200 |  |
| P. aeruginosa | 31.36 ± 0.937 | 12 | 0.9836 |
|  | 27.51 ± 0.264 | 102 |  |
|  | 24.24 ± 0.150 | 1017 |  |
|  | 20.68 ± 0.215 | 10 166 |  |

The data presented in the table above show that the lysis of the tested microorganisms is linear using the sonication instrument.

The invention claimed is:

1. An apparatus for performing sonication on liquid samples, comprising:
   a rack (1) for holding an array of sample vials (2);
   an ultrasonic probe (3) with an arrangement of recesses (4) corresponding to the array of sample vials (2) and adapted to respectively receive and contact an outer surface of a bottom portion (2a) of a respective one of the sample vials (2); and
   a counter-holder (5) with an arrangement of pushing members (6) corresponding to the array of sample vials (2) and adapted to respectively apply a force to a respective one of the sample vials (2) so as to push the bottom portion (2a) of each vial (2) into contact with the associated recess (4) of the probe (3), and
   wherein the pushing members are in the form of pushrods (6) and are arranged to apply the force to a top portion of the respective associated vials (2) wherein the pushrods are elastically biased towards the vials.

2. The apparatus of claim 1, wherein a positioning mechanism (7) is provided to selectively engage the pushing members (6) with the vials (2).

3. The apparatus of claim 2, wherein the positioning mechanism (7) comprises a platform (8) for holding the array of pushing members (6), said platform (8) being supported so as to be at least movable in the direction towards and away from the probe (3) and including a drive mechanism for alternatingly moving the platform (8) in this direction.

4. The apparatus of claim 1, wherein the rack (1) is movably supported in the direction of the center axes and elastically biased in a direction towards the pushing members (6).

5. The apparatus of claim 1, further comprising a moving mechanism for moving the rack (1) between a position outside of a housing of the apparatus and a position inside the housing aligned with the ultrasonic probe (3).

6. The apparatus of claim 1, wherein the recesses (4) are formed to match a bottom configuration of the vials (2) in the array.

7. The apparatus of claim 6, wherein each recess (4) is configured so as to match different bottom configurations of at least two different vials (2).

8. The apparatus of claim 6, wherein at least the portion of the probe (3) containing the recesses (4) is exchangeable to accommodate a different array of sample vials (2) and/or sample vials (2) with different bottom configuration.

9. The apparatus of claim 6, wherein the recesses (4) are rotational symmetrical about a center axis.

10. The apparatus of claim 9, wherein the rotation of the recesses (4) is hemispherical or conical.

11. The apparatus of claim 7, wherein each recess (4) has a rounded bottom portion (4a) and a conical peripheral portion (4b).

12. A method of preparing a sample for detection of cell components, comprising:
    providing the sample in a sample vial (2),
    placing the sample vial (2) in the apparatus as defined in claim 1,
    performing sonication on the sample in the sample vial (2) by the apparatus using the following parameters to effect a lysis of the sample:
    applying a mechanical stress in between the sample vial and the probe of 0.1 to 1 N/mm$^2$,
    applying a peak-to-peak amplitude of vibration of 2 to 10 μm, and
    applying a frequency of vibration of 20 to 100 kHz.

13. The method of claim 12, wherein plural samples are provided in plural sample vials in the array and the sonication is simultaneously performed in the apparatus on the plural samples in the array.

14. The method of claim 12, wherein the sample(s) is/are provided in a sample volume of 20 μl to 1 ml in sample vial(s) having a rated volume of 200 μl to 50 ml.

15. The method of claim 12, wherein the sample vial(s) used for receiving the sample(s) is/are standard laboratory tubes.

16. The method of claim 12, wherein the sample vial(s) are conical laboratory tubes.

17. The method of claim 16, wherein the sample vial(s) are made from a plastic material, which is polypropylene, polystyrene, polycarbonate, or polyethylene material.

18. The method of claim 16, wherein the sample vial(s) are made from 50 ml conical centrifuge tubes, round-bottom tubes, 1.5 ml microcentrifuge tubes, 2 ml microcentrifuge tubes, multi-well plates, or microtiter plates.

* * * * *